(12) United States Patent
Ritzberger et al.

US008778075B2

(10) Patent No.: US 8,778,075 B2
(45) Date of Patent: Jul. 15, 2014

(54) LITHIUM SILICATE GLASS CERAMIC AND GLASS WITH ZRO2 CONTENT

(71) Applicant: Ivoclar Vivadent AG, Schaan (LI)

(72) Inventors: Christian Ritzberger, Grabs (CH); Ricardo Dellagiacomo, Feldkirch-Gisingen (AT); Marcel Schweiger, Chur (CH); Harald Bürke, Frastanz (AT); Wolfram Höland, Schaan (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 13/958,916

(22) Filed: Aug. 5, 2013

(65) Prior Publication Data

US 2013/0323404 A1    Dec. 5, 2013

Related U.S. Application Data

(63) Continuation of application No. 13/079,861, filed on Apr. 5, 2011, now Pat. No. 8,536,078.

(30) Foreign Application Priority Data

Apr. 16, 2010   (EP) .................................... 10160222

(51) Int. Cl.
  *A61K 6/027*   (2006.01)
  *C03C 10/04*   (2006.01)
(52) U.S. Cl.
  USPC .......... 106/35; 501/7; 501/5; 501/64; 501/68; 501/69; 501/72; 433/202.1; 433/212.1; 428/689; 428/699
(58) Field of Classification Search
  USPC ............ 106/35; 65/33.1; 501/7, 5, 64, 68, 69, 501/72
  See application file for complete search history.

(56) References Cited

U.S. PATENT DOCUMENTS

| | | | |
|---|---|---|---|
| 3,006,775 A | 10/1961 | Chen | |
| 4,155,888 A | 5/1979 | Mooth et al. | |
| 5,176,961 A | 1/1993 | Crooker et al. | |
| 5,219,799 A | 6/1993 | Beall et al. | |
| 5,432,130 A | 7/1995 | Rheinberger et al. | |
| 5,507,981 A | 4/1996 | Petticrew et al. | |
| 5,618,763 A | 4/1997 | Frank et al. | |
| 5,691,256 A | 11/1997 | Taguchi et al. | |
| 5,698,019 A | 12/1997 | Frank et al. | |
| 5,698,482 A | 12/1997 | Frank et al. | |
| 5,702,514 A | 12/1997 | Petticrew et al. | |
| 5,872,069 A | 2/1999 | Abe et al. | |
| 5,968,856 A | 10/1999 | Schweiger et al. | |
| 6,048,589 A * | 4/2000 | Suzuki et al. | 427/554 |
| 6,121,175 A | 9/2000 | Drescher et al. | |
| 6,174,827 B1 | 1/2001 | Goto et al. | |
| 6,270,876 B1 | 8/2001 | Abe et al. | |
| 6,420,288 B2 * | 7/2002 | Schweiger et al. | 501/7 |
| 6,455,451 B1 | 9/2002 | Brodkin et al. | |
| 6,514,893 B1 | 2/2003 | Schweiger et al. | |
| 6,593,257 B1 | 7/2003 | Nagata et al. | |
| 7,316,740 B2 | 1/2008 | Schweiger et al. | |
| 7,452,836 B2 | 11/2008 | Apel et al. | |
| 8,536,078 B2 * | 9/2013 | Ritzberger et al. | 501/6 |
| 2002/0009600 A1 | 1/2002 | Peng et al. | |
| 2002/0022563 A1 | 2/2002 | Schweiger et al. | |
| 2002/0031670 A1 | 3/2002 | Goto et al. | |
| 2002/0035025 A1 | 3/2002 | Schweiger et al. | |
| 2005/0127544 A1 | 6/2005 | Brodkin et al. | |
| 2009/0023574 A1 | 1/2009 | Holand et al. | |
| 2009/0256274 A1 | 10/2009 | Castillo | |
| 2011/0030423 A1 | 2/2011 | Johannes et al. | |
| 2011/0256409 A1 | 10/2011 | Ritzberger et al. | |
| 2012/0248642 A1 | 10/2012 | Ritzberger et al. | |
| 2012/0309607 A1 * | 12/2012 | Durschang et al. | 501/59 |

FOREIGN PATENT DOCUMENTS

| | | | |
|---|---|---|---|
| CA | 2252660 | * | 5/1990 |
| CA | 2252660 A1 | | 5/1999 |
| EP | 0231773 A1 | | 8/1987 |
| EP | 1688398 A1 | | 8/2006 |
| GB | 2284655 A | | 6/1995 |
| JP | 2001035417 A | | 2/2001 |
| JP | 2005062832 A | | 3/2005 |
| WO | 2012143147 A1 | | 10/2012 |

OTHER PUBLICATIONS

Glassi et al, "Injection moulding of LiO2-ZrO2-SiO2-Al2O3 (LZSA) glass ceramics", Glass Technol. vol. 46 (3), Jun. 2005, pp. 277-280.*
Giassi et al., Injection moulding of Li2O-ZrO2-SiO2-Al2O3 (LZSA) glass ceramics, Glass Tech., Jun. 2005, vol. 46, No. 3, pp. 277-280.
Montedo, O.R.K, et al., Low Thermal Expansion Sintered LZSA Glass-Ceramics, American Ceramic Society Bulletin, 2008, vol. 87, No. 7, pp. 34-40.

* cited by examiner

*Primary Examiner* — Carol M Koslow
(74) *Attorney, Agent, or Firm* — Ann M. Knab; Thad McMurray (57) ABSTRACT

Lithium silicate glass ceramics and glasses are described which can advantageously be applied to zirconium oxide ceramics in particular by pressing-on in the viscous state and form a solid bond with these.

45 Claims, 4 Drawing Sheets

LITHIUM SILICATE GLASS CERAMIC AND GLASS WITH ZRO2 CONTENT

CROSS-REFERENCE TO RELATED APPLICATIONS

This application is a continuation of U.S. application Ser. No. 13/079,861, filed Apr. 5, 2011, now U.S. Pat. No. 8,536,078, which claims the benefit of European Patent Application Serial No. 10160222.5, filed Apr. 16, 2010, all which are hereby incorporated by reference in their entirety.

TECHNICAL FIELD

The invention relates to lithium silicate glass ceramic and glass which comprise $ZrO_2$ and are suitable in particular for coating zirconium oxide ceramic.

BACKGROUND OF THE INVENTION

Zirconium oxide ceramics are characterized by excellent biocompatibility and outstanding mechanical properties, which is why in the past they have increasingly been used as a material for implants and prostheses, but also as framework materials for dental restorations. Ceramics based on partially stabilized zirconium oxide are primarily used for this.

In many cases it is desirable to alter the surface of the zirconium oxide ceramic by coating it with a different material. Specifically when preparing dental restorations based on zirconium oxide ceramic, such a coating is regularly used to give the restoration the desired visual properties.

Glass ceramics have already been used in the past to coat or veneer oxide ceramics, such as zirconium oxide ceramics. These include feldspar-based ceramics or fluoroapatite glass ceramics.

Lithium disilicate glass ceramics are also known which, because of their high translucency and very good mechanical properties, are used in particular in the dental field and primarily for preparing dental crowns and small bridges.

U.S. Pat. No. 7,316,740, the entirety which is hereby incorporated by reference describes lithium silicate glass ceramics which can additionally contain 0 to 2 wt.-% $ZrO_2$. These are processed into the desired dental restorations in particular in the form of lithium metasilicate glass ceramics by means of CAD/CAM methods, wherein a subsequent heat treatment effects the conversion of the metasilicate phase to the high-strength disilicate phase. The glass ceramics can also be used for pressing over ceramic restorations.

U.S. Pat. No. 7,452,836, the entirety which is hereby incorporated by reference, describes similar lithium silicate glass ceramics which are substantially free of ZnO and in addition to other components can contain 0 to 4 wt.-% $ZrO_2$. To achieve high strengths, however, small quantities of from 0 to 2 wt.-% $ZrO_2$ are preferred. These glass ceramics also serve in particular to prepare dental restorations after mechanical processing by means of CAD/CAM.

However, these lithium silicate glass ceramics known from the state of the art have the disadvantage that they are not suitable for coating zirconium oxide ceramic in particular by means of a pressing-on in the viscous state, since after the pressing-on in the viscous flow process cracks and flaws form in the glass ceramic. Thus, such a composite does not have the mechanical properties that are indispensable specifically for use as dental restoration material.

Glass ceramics with lithium disilicate as the main crystal phase which are to be suitable for veneering dental restorations comprising yttrium-stabilized zirconium dioxide are also known from U.S. Published Application No. 2011030423, the entirety which is hereby incorporated by reference. However, these glass ceramics contain quantities of only up to 6.0 wt.-% of $ZrO_2$ and substantial quantities of $Na_2O$. The $ZrO_2$ present acts merely as a standard nucleating agent together with an optionally present further nucleating agent such as $TiO_2$ in order to effect the formation of the desired lithium disilicate crystal phase.

SUMMARY OF THE INVENTION

In view of the above-described disadvantages of the already known glass ceramics, the object of the invention is to provide a glass ceramic which can be coated onto a zirconium oxide ceramic in particular by pressing it on in the viscous state and in the process forming a coating substantially free of cracks and flaws. Moreover, the glass ceramic should be capable of forming a solid bond with the zirconium oxide ceramic to be coated, and it should have visual and mechanical properties enabling it to be used in particular as a coating material for dental restorations but also as a material for preparing dental restorations.

The lithium silicate glass ceramic according to the invention is characterized in that it comprises at least 6.1 wt.-% $ZrO_2$ and in particular at least 6.5, preferably at least 7.0 and particularly preferably at least 8.0 wt.-% $ZrO_2$, and more particularly preferred at least 10.0 wt.-% $ZrO_2$.

In a further preferred embodiment, the glass ceramic comprises in particular 6.1 to 20.0 wt.-%, preferably 8.0 to 20.0 wt.-%, particularly preferably 8.0 to 18.0 wt.-% and quite particularly preferably 10.0 to 16.0 wt.-% $ZrO_2$.

Further, a glass ceramic which comprises 55.0 to 71.0 and in particular 60 to 69 wt.-% $SiO_2$ is preferred.

In addition, a glass ceramic which comprises 9.0 to 17.0 and in particular 11 to 15 wt.-% $Li_2O$ is preferred.

Furthermore, it has proven preferable if the glass ceramic comprises a nucleating agent selected from Pt, Pd, Au, Ag, or mixtures thereof. It has proven particularly preferable if the glass ceramic comprises 0.5 to 12.0 and in particular 2.5 to 7.0 wt.-% nucleating agents. Preferred nucleating agents are selected from $P_2O_5$, $TiO_2$, $Nb_2O_5$, metals, e.g. Pt, Pd, Au and Ag, or mixtures thereof. Particularly preferably, the glass ceramic comprises $P_2O_5$ as nucleating agent. Surprisingly, $P_2O_5$ as nucleating agent in particular effects the formation of desired lithium disilicate crystals while largely preventing the formation of $ZrO_2$-containing crystal phases which could cause a substantial deterioration in translucency. Through its use the formation of other undesired secondary crystal phases is apparently also largely prevented.

The glass ceramic according to the invention preferably comprises a further alkali metal oxide in a quantity of from 1.0 to 7.0, preferably 2.0 to 7.0 and particularly preferably 2.0 to 5.0 wt.-%. The term "further alkali metal oxide" denotes alkali metal oxide with the exception of $Li_2O$. The further alkali metal oxide is in particular $K_2O$, $Cs_2O$ and/or $Rb_2O$ and is particularly preferably $K_2O$. It is assumed that the use of $K_2O$ contributes to the strengthening of the glass network compared with the $Na_2O$ used in conventional glass ceramics. It is preferred that the glass ceramic comprises less than 2.0, in particular less than 1.0, preferably less than 0.5 and particularly preferably essentially no $Na_2O$.

It is further preferred that the glass ceramic comprises up to 5.0 wt.-% alkaline earth metal oxide, wherein the alkaline earth metal oxide is in particular CaO, BaO, MgO, SrO or a mixture thereof.

Further, a glass ceramic which comprises 0.2 to 10.0, in particular 2.5 to 7.0 and preferably 2.5 to 3.5 wt.-% oxide of trivalent elements is preferred, wherein this oxide is selected in particular from $Al_2O_3$, $Y_2O_3$, $La_2O_3$, $Bi_2O_3$ and mixtures thereof, and preferably is $Al_2O_3$.

A glass ceramic which comprises at least one and preferably all of the following components is particularly preferred:

| Component | wt.-% |
| --- | --- |
| $SiO_2$ | 55.0 to 71.0 |
| $Li_2O$ | 9.0 to 17.0 |
| $K_2O$ | 1.0 to 7.0, in particular 2.0 to 5.0 |
| $Al_2O_3$ | 0.5 to 5.0, in particular 2.5 to 3.5 |
| $P_2O_5$ | 0.5 to 12.0, in particular 2.5 to 7.0 |
| $ZrO_2$ | 6.1 to 20.0, in particular 8.0 to 20.0. |

The glass ceramic according to the invention can moreover also comprise additional components which are selected in particular from further oxides of tetravalent elements, further oxides of pentavalent elements, oxides of hexavalent elements, melt accelerators, colourants and fluorescent agents.

The term "further oxides of tetravalent elements" denotes oxides of tetravalent elements with the exception of $SiO_2$ and $ZrO_2$. Examples of further oxides of tetravalent elements are $SnO_2$ and $GeO_2$.

The term "further oxides of pentavalent elements" denotes oxides of pentavalent elements with the exception of $P_2O_5$. An example of a further oxide of pentavalent elements is $Bi_2O_5$.

Examples of oxides of hexavalent elements are $WO_3$ and $MoO_3$.

A glass ceramic which comprises at least one further oxide of tetravalent elements, one further oxide of pentavalent elements or one oxide of hexavalent elements is preferred.

Examples of melt accelerators are fluorides.

Examples of colourants and fluorescent agents are oxides of d- and f-elements, such as e.g. the oxides of Ti, Sc, Mn, Fe, Ag, Ta, W, Ce, Pr, Nd, Tb, Er and Yb.

The term "main crystal phase" used below denotes the crystal phase which has the highest proportion by volume compared with other crystal phases.

The glass ceramic according to the invention preferably comprises lithium metasilicate as main crystal phase. In particular the glass ceramic comprises more than 10 vol.-%, preferably more than 20 vol.-% and particularly preferably more than 30 vol.-% of lithium metasilicate crystals, relative to the total glass ceramic.

In a further preferred embodiment, the glass ceramic comprises lithium disilicate as main crystal phase. In particular the glass ceramic comprises more than 10 vol.-%, preferably more than 20 vol.-% and particularly preferably more than 30 vol.-% of lithium disilicate crystals, relative to the total glass ceramic.

BRIEF DESCRIPTION OF THE FIGURES

Further advantages, details and features emerge from the following description of embodiments of the invention on the basis of the drawings, in which.

DETAILED DESCRIPTION

The lithium disilicate glass ceramic according to the invention shows particularly good mechanical properties and can be produced by heat treatment of the lithium metasilicate glass ceramic according to the invention.

It was surprisingly shown that, despite its high $ZrO_2$ content, the lithium disilicate glass ceramic according to the invention has advantageous mechanical parameters, such as high fracture toughness values, and can be applied to zirconium oxide ceramic in the viscous state by sintering-on or in particular pressing-on, without resultant stresses in the glass ceramic which manifest themselves in cracks or flaws. It is particularly surprising that these very good mechanical properties are achieved although the structure of the glass ceramic has lithium disilicate crystals which are not normally cross-linked to one another. On the other hand, such a cross-linking occurs with the known lithium disilicate glass ceramics and it is regarded as a key reason for their high strengths. It is currently assumed that the $ZrO_2$ in the glass ceramic according to the invention, unlike in known products, does not serve as a nucleating agent for other crystal phases, but rather strengthens the glass network via Zr—O polyhedra embedded therein. These polyhedra can be $[ZrO_{6/2}]^{2-}$ or $[ZrO_{2/2}]^{4-}$ structural units which function as network formers or network modifiers.

It is also surprising that, despite its high $ZrO_2$ content, the lithium disilicate glass ceramic according to the invention has a high translucency and that no amorphous-amorphous phase separation occurs and that it can thus be used for the aesthetically pleasing coating of in particular dental restorations based on zirconium oxide ceramic.

The lithium disilicate crystals present in the lithium disilicate glass ceramic according to the invention have in particular the form of small plates. It is assumed that this special morphology allows the crack-free material bond with zirconium oxide ceramics. The build-up of critical stresses in the material bond during the thermal cooling phase seems to be less strongly pronounced in the small-plate shaped crystal form than in lithium disilicate glass ceramics with elongated or needle-shaped crystals. In addition, a good fracture toughness, expressed by the $K_{IC}$ value, is achieved with the small-plate shaped crystal morphology.

The lithium disilicate glass ceramic according to the invention has in particular a fracture toughness, measured as $K_{IC}$ value, of at least 1.5 MPa·m$^{0.5}$ and in particular more than 1.8 MPa·m$^{0.5}$. Furthermore, it has a high biaxial fracture toughness of preferably from 200 to 500 MPa. Moreover, it shows a high chemical resistance which was determined by mass loss after storage in acetic acid. The chemical resistance is in particular less than 60 μg/cm$^2$. Finally, it has a linear coefficient of thermal expansion of in particular less than $10.3 \times 10^{-6} K^{-1}$ m/m, measured in the range of from 100 to 500° C., which is thus as a rule smaller than that of the zirconium oxide ceramic to be coated.

The invention also relates to a lithium silicate glass with nuclei that are suitable for forming lithium metasilicate and/or lithium disilicate crystals, wherein the glass comprises the components of the above-described glass ceramics according to the invention. This glass thus comprises at least 6.1 wt.-% $ZrO_2$. With regard to preferred embodiments of this glass, reference is made to the above-described preferred embodiments of the glass ceramics according to the invention.

The glass with nuclei according to the invention can be produced by heat treatment of a correspondingly composed starting glass, which forms a further aspect of the present invention. By a further heat treatment the lithium metasilicate glass ceramic according to the invention can then be formed, which in turn can be converted into the lithium disilicate glass ceramic according to the invention by further heat treatment. The starting glass, the glass with nuclei and the lithium metasilicate glass ceramic can consequently be seen as precursors for the production of the high-strength lithium disilicate glass ceramic.

The glass ceramic according to the invention and the glass according to the invention are present in particular in the form of powders or blanks, as they can easily be further processed in these forms. They can, however, also be present in the form of dental restorations, such as inlays, onlays, crowns or abutments.

The invention also relates to a process for preparing the glass ceramic according to the invention and the glass with nuclei according to the invention, in which a starting glass with the components of the glass ceramic or the glass is subjected to at least one heat treatment in the range of from 450 to 950° C.

The starting glass therefore comprises at least 6.1 wt.-% $ZrO_2$. In addition, it preferably also comprises suitable quantities of $SiO_2$ and $Li_2O$ in order to make the formation of a lithium silicate glass ceramic possible. Furthermore, the starting glass can also comprise further components, such as are given above for the lithium silicate glass ceramic according to the invention. Those embodiments are preferred which are also stated as preferred for the glass ceramic.

To prepare the starting glass, the procedure is in particular that a mixture of suitable starting materials, such as e.g. carbonates, oxides, phosphates and fluorides, is melted at temperatures of in particular from 1300 to 1600° C. for 2 to 10 h. To achieve a particularly high homogeneity, the obtained glass melt is poured into water in order to form a glass granulate, and the obtained granulate is then melted again.

The melt can then be poured into moulds to produce blanks of the starting glass, so-called solid glass blanks or monolithic blanks.

It is also possible to pour the melt into water again in order to prepare a granulate. This granulate can then be pressed, after grinding and optionally adding of further components, such as colourants and fluorescent agents, to form a blank, a so-called powder green compact.

Finally, the starting glass can also be processed to form a powder after granulation.

The starting glass is then subjected, e.g. in the form of a solid glass blank, a powder green compact or in the form of a powder, to at least one heat treatment in the range of from 450 to 950° C. It is preferred that a first heat treatment is initially carried out at a temperature in the range of from 500 to 600° C. to prepare a glass according to the invention with nuclei which are suitable for forming lithium metasilicate and/or lithium disilicate crystals. This glass can then preferably be subjected to at least one further temperature treatment at a higher temperature and in particular more than 570° C. to effect crystallization of lithium metasilicate or lithium disilicate.

The at least one heat treatment carried out in the process according to the invention can also take place during the pressing or sintering of the glass according to the invention or the glass ceramic according to the invention onto the selected zirconium oxide ceramic.

Dental restorations, such as inlays, onlays, crowns or abutments, can be prepared from the glass ceramic according to the invention and the glass according to the invention. The invention therefore also relates to their use for the preparation of dental restorations.

The glass ceramic according to the invention and the glass according to the invention are, however, suitable in particular for coating zirconium oxide ceramics. The invention is therefore also directed towards the use of the glass according to the invention or the glass ceramic according to the invention for coating zirconium oxide ceramics.

The invention also relates to a process for coating zirconium oxide ceramic, in which the glass ceramic according to the invention or the glass according to the invention is applied to the zirconium oxide ceramic and is subjected to increased temperature.

This can take place in particular by sintering-on and preferably by pressing-on. With the sintering-on, the glass ceramic or the glass is applied to the ceramic to be coated in the usual way, e.g. as powder, and then sintered at increased temperature. With the preferred pressing-on, the glass ceramic according to the invention or the glass according to the invention is pressed on, e.g. in the form of powder green compacts or monolithic blanks, at an increased temperature of e.g. from 700 to 1200° C., applying pressure, e.g. 2 to 10 bar. The methods described in EP 231 773, the entirety which is hereby incorporated by reference, and the press furnace disclosed there can be used in particular for this. A suitable furnace is e.g. the Programat EP 5000 from Ivoclar Vivadent AG, Liechtenstein.

It is preferred that, after conclusion of the coating process, the glass ceramic according to the invention is present with lithium disilicate as main crystal phase, as it has particularly good properties. It is surprisingly shown that the glass ceramic according to the invention has practically no flaws and cracks once it has been coated onto the zirconium oxide ceramic, and a solid bond between glass ceramic and ceramic is achieved.

It is preferred that the zirconium oxide ceramic comprises at least one oxide of Ce, Y, Sr, Ca or Mg for stabilizing the tetragonal phase. The zirconium oxide ceramic can also be present in the form of a composite with other inorganic components.

The zirconium oxide ceramic coated with the glass ceramic according to the invention or the glass according to the invention forms a further subject of the invention.

In view of the above-described properties of the glass ceramic according to the invention and the glass according to the invention as its precursor, they are also suitable in particular for use in dentistry. A subject of the invention is therefore also the use of the glass ceramic according to the invention or the glass according to the invention as a dental material and in particular for preparing dental restorations or as a coating material for dental restorations, such as crowns and bridges.

It is surprising that no cracks in the glass ceramic occur in the bond between the lithium disilicate glass ceramic according to the invention and zirconium oxide ceramic. It is presumed that in particular the special small-plate shaped morphology of the lithium disilicate crystals is of importance for this. The build-up of critical stress in the material bond during the thermal cooling phase seems to be less strongly pronounced in the small-plate shaped crystal form than in lithium disilicate glass ceramics with elongated or needle-shaped crystals. In addition a good fracture toughness of up to 2.1

MPa·m$^{0.5}$ is achieved in particular with the small-plate shaped crystal morphology, although a direct cross-linking of the lithium disilicate crystals is essentially not to be seen in the structure. The coated zirconium oxide ceramic according to the invention is thus a strong compound between high-strength and high-toughness zirconium oxide ceramic on the one hand and tough glass ceramic on the other, which is why this compound can absorb high loads in the chewing cycle. The glass ceramic according to the invention can thus advantageously also be used directly in the coating of long-span bridges with more than three members based on zirconium oxide ceramic.

The invention is described in further detail below with reference to examples.

EXAMPLES

Examples 1 to 28

Composition and Crystal Phases

A total of 28 glasses and glass ceramics according to the invention with the composition given in tables I to IV were prepared by melting corresponding starting glasses followed by heat treatment for controlled nucleation and crystallization.

For this, the starting glasses were firstly melted in a 100 to 200 g scale from usual raw materials at 1400 to 1500° C. and transformed into glass frits by pouring them into water. These glass frits were then melted a second time at 1450 to 1550° C. for 1 to 3 h for the homogenization. The obtained glass melts were poured into pre-heated moulds to produce glass monoliths. These glass monoliths were transformed into glasses and glass ceramics according to the invention by thermal treatment.

The applied thermal treatment for the controlled nucleation and controlled crystallization is given in table V for selected examples. The first heat treatment in the range of from 500 to 560° C. usually led to the formation of lithium silicate glasses with nuclei for lithium metasilicate or lithium disilicate crystals, the second heat treatment at 650 to 710° C. to the formation of lithium metasilicate glass ceramics and the third heat treatment in the range of from 800 to 920° C. to the formation of lithium disilicate glass ceramics.

In some examples, a second non-isothermal heat treatment with simultaneous analysis of the formed crystal phases was carried out at the respectively given temperature by high-temperature X-ray diffraction (HT-XRD) after a first heat treatment.

The crystal phases obtained after conclusion of all the heat treatments are also listed in table V. Surprisingly, glass ceramics with lithium disilicate as main crystal phase were always obtained. Examples 5 and 6 were additionally repeated, by carrying out only the first and second heat treatment. In this way, glass ceramics with lithium metasilicate as main crystal phase were produced.

Despite the high $ZrO_2$ content of up to 20 wt.-%, only in example 8 $ZrO_2$ crystallized as secondary crystal phase.

Example 29

Glass and Glass Ceramic Blanks

A glass with the composition according to example 5 was prepared by mixing corresponding raw materials in the form of oxides and carbonates for 30 min in a Turbula mixer and then melting the mixture at 1450° C. for 120 min in a platinum crucible. The melt was poured into water in order to obtain a finely divided glass granulate. This glass granulate material was melted again at 1530° C. for 150 min in order to obtain a glass melt with particularly high homogeneity. The temperature was reduced to 1500° C. for 30 min and cylindrical glass blanks with a diameter of 12.5 mm were then poured into pre-heated, separable steel moulds or graphite moulds. The obtained glass cylinders were then stress-relieved at 550° C. A glass with nuclei for lithium metasilicate or lithium disilicate crystals was obtained.

Figure 1:
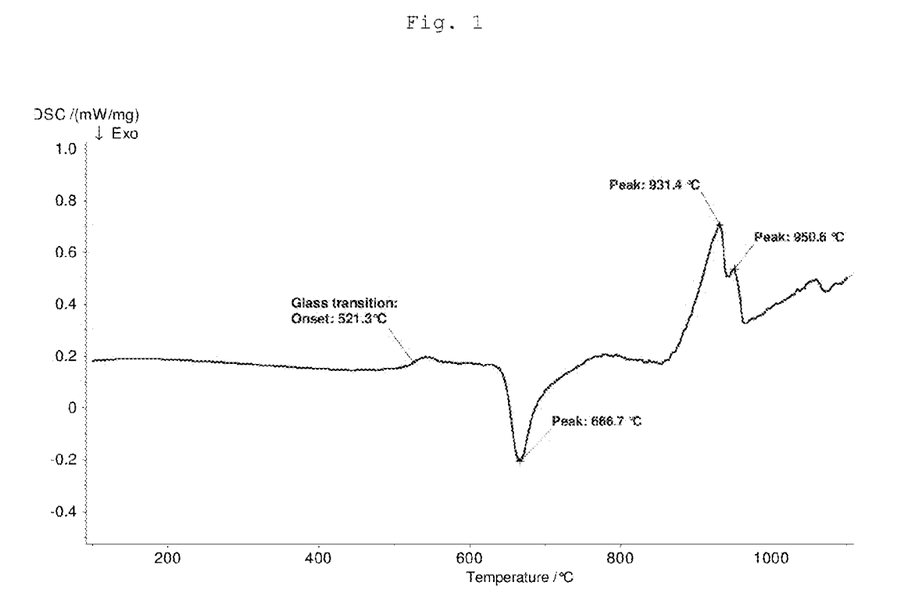
FIG. 1 shows the result of the differential scanning calorimetry (DSC) of a pounded glass cylinder according to Example 29.

FIG. 1 shows the result of the differential scanning calorimetry (DSC) of a pounded glass cylinder.

Figure 2:
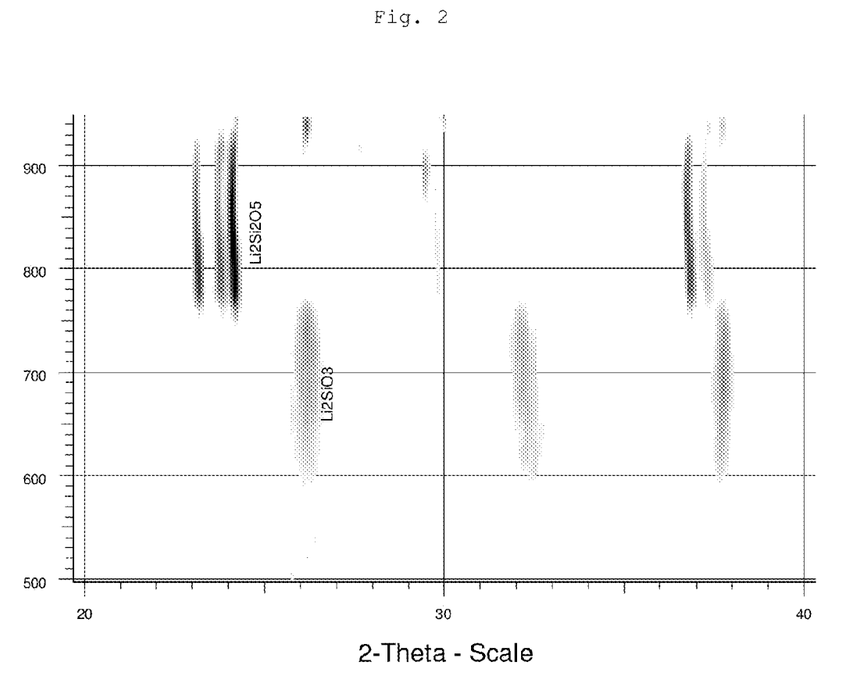
FIG. 2 shows, using high-temperature X-ray diffraction (HT-XRD) of a glass cylinder, the dependence of the formation of lithium metasilicate (Li2SiO3) and lithium disilicate (Li2Si2O5) from the temperature.

FIG. 2 shows, using high-temperature X-ray diffraction (HT-XRD) of a glass cylinder, the dependence of the formation of lithium metasilicate (Li2SiO3) and lithium disilicate (Li2Si2O5) from the temperature.

The glass cylinders were then subjected to a first crystallization at 680 to 700° C. for 20 min. The heating rate was 15° C. per minute. The glass cylinders were then subjected to a second crystallization at 850 to 880° C. for 30 min. After this treatment, the crystal phase analysis showed a glass ceramic according to the invention with lithium disilicate as main crystal phase as well as small proportions of lithium metasilicate and lithium phosphate as secondary phases.

Figure 3:
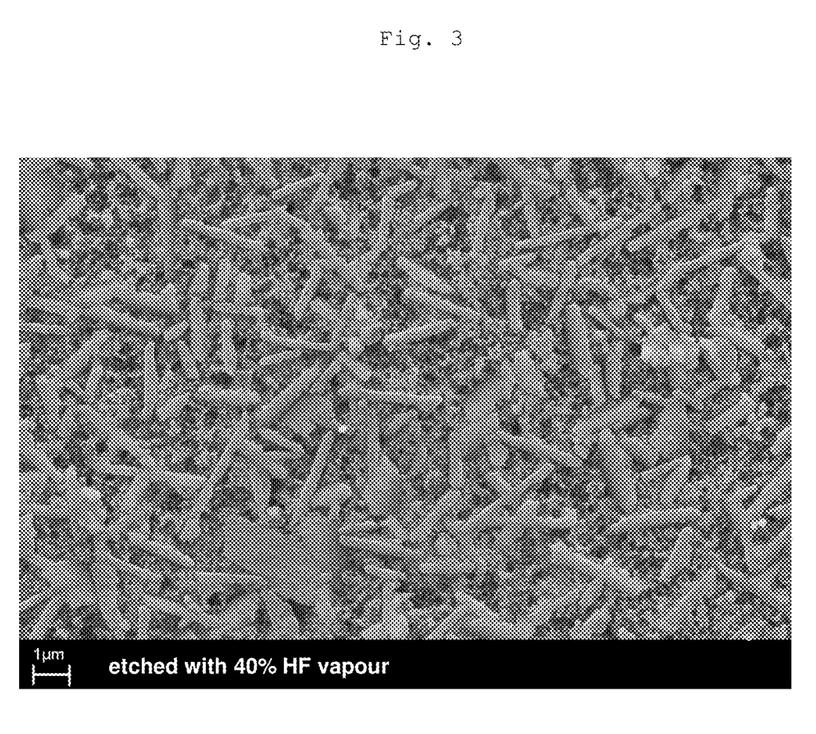
FIG. 3 shows a scanning electron microscopy (SEM) photograph of a crystallized cylinder of Example 29 which has been polished and etched for 30 s with HF vapour.

FIG. 3 shows a scanning electron microscopy (SEM) photograph of a crystallized cylinder which has been polished and etched for 30 s with HF vapour.

The crystallized cylinders were moreover further processed by hot-pressing at a pressing temperature of 910° C. using an EP600 press furnace, Ivoclar Vivadent AG, to form testpieces. The properties of these testpieces were as follows:

| | |
|---|---|
| Colour: | white, translucent without fluorescence |
| Solubility: | 24 µg/cm$^2$ (according to ISO 6872 of Sep. 1, 2008) |
| Biaxial strength: | 420 MPa (according to ISO 6872 of Sep. 1, 2008) |
| Fracture toughness: | 2.0 MPam$^{0.5}$ (determined as $K_{IC}$ value using the SEVNB method according to ISO 6872 of Sep. 1, 2008) |
| Coefficient of thermal expansion: | 9.9 * 10$^{-6}$ * 1/K (in the range 100 to 500° C.) |

Example 30

Hot-Pressing onto Zirconium Oxide Ceramic

The lithium disilicate glass ceramic according to example 5 was pressed by hot-pressing at 920° C. onto zirconium oxide ceramic of the type 3 Y-TZP, obtainable from Tosoh, in a Programat EP 5000 combined press and firing furnace from Ivoclar Vivadent AG, Liechtenstein. After conclusion of the coating process, a defect-free join resulted.

Figure 4:
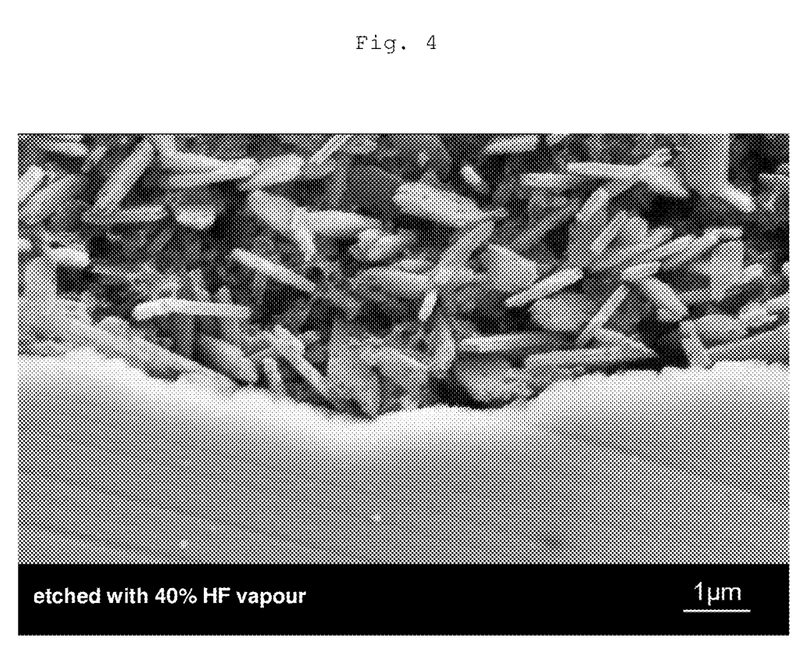
FIG. 4 shows a scanning electron microscopy (SEM) photograph of the bond between a lithium disilicate glass ceramic according to Example 5 and a zirconium oxide ceramic after etching with 40% HF vapour.

FIG. 4 shows a scanning electron microscopy (SEM) photograph of this bond after etching with 40% HF vapour.

Example 31

Hot-Pressing onto Small Tooth Caps and Bridge Frameworks

Single small tooth caps and four-element bridge frameworks of densely sintered zirconium oxide (e.max ZirCAD, Ivoclar Vivadent AG) were made up into anatomically shaped restorations with a plastic that can be burned out (PMMA).

Both the bridge frameworks and the plastic parts were manufactured by CAD/CAM processes, whereby a reproducible geometry and layer thickness were able to be achieved. The restorations were invested in dental investment compound (IPS PressVest Speed, Ivoclar Vivadent AG), the plastic was burned out and the crystallized cylinders according to example 29 were pressed directly onto the frameworks at a temperature of 910° C. No intermediate layer (liner) was applied to the zirconium oxide.

After the complete cooling, the articles were devested with a sandblaster, wherein no special precaution was necessary, because of the high strength of the coated-on glass ceramic. The articles were separated from the compression channels, reworked dry with a diamond grinder, and then treated for 20 min with IPS INVEX Liquid (Ivoclar Vivadent AG) under ultrasound, in order to loosen any remaining residues of investment compound, which were then sandblasted with $Al_2O_3$ sand with a grain size of 100 μm at 1-2 bar pressure.

The surface was cleaned with hot steam and glazed twice with IPS e.max Ceram Glaze (Ivoclar Vivadent AG) at 770° C., whereby an attractive gloss was produced. No special cooling (relaxation cooling) was applied during the glazing firing. The thus-prepared restorations, i.e. crowns and bridges, were aesthetically pleasing and defect-free. They showed no cracks, bubbles or raised areas. After sawing, an excellent bond between the coated-on lithium disilicate glass ceramic according to the invention and the zirconium oxide was recognizable by means of SEM in the cross-section.

In each case 8 crowns and 8 bridges were subjected to thermocycling of from 5 to 55° C. in a chewing machine (Willitec) with 300,000 cycles while stored in water. The test strength was 30, 60 or 90 N during every 100,000 cycles. The load was applied with a frequency of 0.8 Hz. There were no chippings at all in the veneer structure.

Example 32

Glass and Glass Ceramic Blanks

Example 29 was repeated with the difference that a glass with the composition according to example 23 was used as a starting material. The obtained crystallized cylinders were further processed into testpieces by hot-pressing at a temperature of 905° C. The properties of these testpieces were as follows:

Colour: tooth coloured, translucent with tooth-like fluorescence

Solubility: 30 μg/cm2 (according to ISO 6872 of Sep. 1, 2008)

Biaxial strength: 405 MPa (according to ISO 6872 of Sep. 1, 2008)

Coefficient of thermal expansion: 9.9*10-6*1/K (in the range 100 to 500° C.)

Example 33

Hot-Pressing onto Small Tooth Caps and Bridge Frameworks

Example 31 was repeated with the difference that the crystallized cylinders according to example 32 were used. After up to four final glazing firings, crowns and bridges were obtained which again showed no cracks, bubbles or raised areas.

Example 34

Glass Ceramic Blank (Powder Green Compact)

Analogously to examples 1 to 28, a starting glass with the composition according to example 24 was melted twice. However, the glass was then not poured into steel moulds, but quenched in water in order to obtain a finely divided glass granulate. The glass granulate material was thermally treated at 550° C. for 20 min and then at 680° C. for 20 min in order to effect the nucleation and the first crystallization. The thus pre-treated granulate was dry-ground to an average grain size of 20 μm and mixed with 0.1 wt.-% of a ceramic colouring pigment. The mixture was moistened with some water and pressed to form a powder green compact at a pressing pressure of 20 MPa. The powder green compact was sintered at 850° C. for 30 min. The crystal phase analysis of the sintered blank showed lithium disilicate as main crystal phase as well as in each case small proportions of lithium metasilicate and lithium phosphate as secondary phases.

The sintered blanks were further processed into testpieces by hot-pressing at 905° C. using the EP600 press furnace (Ivoclar Vivadent AG). The properties of the testpieces were as follows:

Colour: tooth coloured, translucent and tooth-like fluorescence

Biaxial strength: 302 MPa (according to ISO 6872 of Sep. 1, 2008)

Example 35

Hot-Pressing onto Small Tooth Caps

Example 31 was repeated with the difference that the sintered blanks according to example 34 were used to compress over small tooth caps. After two final glazing firings, crowns were obtained which again showed no cracks, bubbles or raised areas.

Example 36

Sintering onto Small Tooth Caps

Analogously to example 34, glass ceramic powder of the composition according to example 24 coloured with 0.1 wt.-% pigment was prepared. However, this time, no powder blanks were pressed. The powder was blended with a modelling liquid (e.max Ceram Build Up Liquid, Ivoclar Vivadent AG) and the mixture was applied to a prefabricated zirconium oxide single small tooth cap in order to model an occlusal morphology. The coated-on mixture was then sintered in a dental furnace (P500, Ivoclar Vivadent AG) at a holding temperature of 850° C. and with a residence time of 2 min.

After the sintering-on, the crowns were trimmed with diamond grinders and coated a second time. Two further glazing firings then took place at a temperature of 770° C. Aesthetically high-quality tooth-coloured crowns with natural-looking fluorescence and opalescence resulted. These also showed no cracks, bubbles or raised areas.

TABLE I

|  | 1 | 2 | 3 | 4 | 5 | 6 | 7 | 8 | 9 |
|---|---|---|---|---|---|---|---|---|---|
| $SiO_2$ | 63.8 | 69.3 | 67.9 | 66.4 | 65.0 | 63.5 | 62.0 | 60.5 | 61.2 |
| $K_2O$ | 3.0 | 3.8 | 3.7 | 3.6 | 3.5 | 3.4 | 3.4 | 3.3 | 0.8 |
| $Li_2O$ | 13.6 | 14.4 | 14.1 | 13.8 | 13.5 | 13.2 | 12.9 | 12.6 | 13.0 |
| $Al_2O_3$ | 3.0 | 3.3 | 3.2 | 3.2 | 3.1 | 3.0 | 2.9 | 2.9 | 1.0 |
| $P_2O_5$ | 3.0 | 3.1 | 3.1 | 3.0 | 2.9 | 2.9 | 2.8 | 2.7 | 4.0 |
| $ZrO_2$ | 9.6 | 6.1 | 8.0 | 10.0 | 12.0 | 14.0 | 16.0 | 18.0 | 20.0 |
| $MoO_3$ | 4.0 | | | | | | | | |
|  | 100.0 | 100.0 | 100.0 | 100.0 | 100.0 | 100.0 | 100.0 | 100.0 | 100.00 |

TABLE II

|  | 10 | 11 | 12 | 13 | 14 | 15 | 16 | 17 | 18 | 19 | 20 |
|---|---|---|---|---|---|---|---|---|---|---|---|
| $SiO_2$ | 69.8 | 64.1 | 65.2 | 60.5 | 64.5 | 64.4 | 66.4 | 55.0 | 70.1 | 64.3 | 64.2 |
| $K_2O$ | 2.0 | 5.0 | 3.5 | 3.3 | 2.0 | 2.0 |  | 4.0 | 3.6 | 3.0 | 1.0 |
| $Li_2O$ | 16.0 | 13.3 | 12.0 | 15.0 | 13.4 | 13.5 | 13.6 | 15.0 | 9.0 | 13.2 | 13.2 |
| $Na_2O$ |  |  |  |  |  |  |  |  | 0.1 |  |  |
| CaO |  |  |  |  | 2.0 |  |  | 2.0 |  |  |  |
| MgO |  |  |  |  |  |  |  |  | 0.1 |  |  |
| SrO |  |  |  |  |  | 2.0 |  |  | 0.1 |  | 1.0 |
| $Al_2O_3$ | 0.2 | 5.0 | 3.1 | 2.9 | 2.0 | 2.0 | 3.0 | 4.0 | 3.5 | 2.9 | 0.5 |
| $La_2O_3$ |  |  |  |  | 6.5 |  |  |  |  |  |  |
| $Y_2O_3$ |  |  |  |  |  | 6.5 |  |  |  |  | 6.5 |
| $P_2O_5$ | 3.3 | 2.9 | 4.1 | 5.0 | 3.5 | 3.5 | 3.0 | 12.0 | 3.5 | 2.9 | 3.5 |
| $ZrO_2$ | 8.6 | 9.7 | 12.1 | 13.3 | 6.1 | 6.1 | 10.0 | 8.0 | 10.0 | 9.7 | 10.1 |
| $Cs_2O$ |  |  |  |  |  |  | 4.0 |  |  | 4.0 |  |
| $VO_2$ | 0.1 |  |  |  |  |  |  |  |  |  |  |
|  | 100.0 | 100.0 | 100.0 | 100.0 | 100.0 | 100.0 | 100.0 | 100.0 | 100.0 | 100.0 | 100.0 |

TABLE III

|  | 21 | 22 | 23 | 24 |
|---|---|---|---|---|
| $SiO_2$ | 61.3 | 62.6 | 64.9 | 64.9 |
| $K_2O$ | 3.3 | 5.0 | 3.5 | 3.5 |
| $Li_2O$ | 12.7 | 12.7 | 13.5 | 13.5 |
| CaO | 3.0 |  |  |  |
| $Al_2O_3$ | 2.9 | 2.9 | 3.1 | 3.1 |
| $P_2O_5$ | 7.0 | 3.5 | 3.0 | 3.0 |
| $ZrO_2$ | 9.0 | 11.3 | 10.4 | 10.9 |
| F | 0.5 |  |  |  |
| $MnO_2$ | 0.2 |  |  |  |
| $Fe_2O_3$ | 0.1 |  |  |  |
| $V_2O_5$ |  |  |  | 0.1 |
| $Tb_4O_7$ |  | 0.4 | 0.5 | 0.5 |
| $CeO2$ |  | 1.3 | 1.0 | 0.6 |
| $Er_2O_3$ |  | 0.3 |  |  |
|  | 100.0 | 100.0 | 100.0 | 100.0 |

TABLE IV

|  | 25 | 26 | 27 | 28 |
|---|---|---|---|---|
| $SiO_2$ | 66.4 | 63.8 | 64.5 | 63.8 |
| $K_2O$ |  | 3.0 | 3.2 | 3.0 |
| $Li_2O$ | 13.6 | 13.6 | 13.8 | 13.6 |
| $Rb_2O$ | 4.0 |  |  |  |
| BaO |  |  | 2.0 |  |
| $Al_2O_3$ | 3.0 | 3.0 | 3.0 | 3.0 |
| $Bi_2O_3$ |  |  |  | 4.0 |
| $P_2O_5$ | 3.0 | 3.0 | 3.5 | 3.0 |
| $ZrO_2$ | 10.0 | 9.6 | 10.0 | 9.6 |
| $WO_3$ |  | 4.0 |  |  |
|  | 100.0 | 100.0 | 100.0 | 100.0 |

TABLE V

| Glass ceramic, no. | Thermal treatment (° C./min) or HT-XRD | Crystal phases MP = main phase SP = secondary phase(s) |
|---|---|---|
| 2 | 500/10, 650/20, 840/7 | MP: $Li_2Si_2O_5$<br>SP: $Li_3PO_4$ $Li_2SiO_3$ |
| 3 | 500/10, 650/20, 840/7 | MP: $Li_2Si_2O_5$<br>SP: $Li_3PO_4$, $Li_2SiO_3$ |
| 4 | 500/10, 650/20, 840/7 | MP: $Li_2Si_2O_5$<br>SP: $Li_3PO_4$, $Li_2SiO_3$; $Li_4SiO_4$ |
| 5 | 540/10, 690/20 | MP: $Li_2SiO_3$<br>SP: none |
| 5 | 540/10, 650/20, 840/7 | MP: $Li_2Si_2O_5$<br>SP: $Li_2SiO_3$; $Li_4SiO_4$ |
| 6 | 540/10, 710/20 | MP: $Li_2SiO_3$<br>SP: none |
| 6 | 540/10, 650/20, 840/7 | MP: $Li_2Si_2O_5$<br>SP: $Li_4SiO_4$ |
| 7 | 560/10 and HT-XRD with cut-out at 860 | MP: $Li_2Si_2O_5$<br>SP: $Li_3PO_4$, $Li_2SiO_3$ |
| 8 | 560/10 and HT-XRD with cut-out at 900 | MP: $Li_2Si_2O_5$,<br>SP: $SiO_2$, $ZrO_2$ |
| 9 | 560/10 and HT-XRD with cut-out at 920 | MP: $Li_2Si_2O_5$,<br>SP: $Li_3PO_4$ |
| 14 | 520/10, 650/20, 800/10 | MP: $Li_2Si_2O_5$<br>SP: $Li_3PO_4$ |
| 15 | 520/10, 650/20, 800/10 | MP: $Li_2Si_2O_5$<br>SP: $Li_3PO_4$, $Li_2SiO_3$ |
| 16 | 520/10, 650/20, 800/10 | MP: $Li_2Si_2O_5$<br>SP: $Li_3PO_4$ |
| 17 | HT-XRD with cut-out at 840 | MP: $Li_2Si_2O_5$<br>SP: $Li_3PO_4$ |
| 25 | 520/10, 650/20, 800/10 | MP: $Li_2Si_2O_5$<br>SP: $Li_3PO_4$ |

TABLE V-continued

| Glass ceramic, no. | Thermal treatment (° C./min) or HT-XRD | Crystal phases MP = main phase SP = secondary phase(s) |
|---|---|---|
| 26 | 520/10, 650/20, 850/10 | MP: Li$_2$Si$_2$O$_5$ SP: Li$_3$PO$_4$, Li$_2$SiO$_3$ |

In the HT-XRD analysis, a heating rate of approx. 2 K/min was used.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. Dental restoration, which is coated with a lithium silicate glass ceramic, wherein the lithium silicate glass ceramic comprises at least 6.1 wt.-% ZrO$_2$.

2. Dental restoration according to claim 1, wherein the lithium silicate glass ceramic comprises 6.1 to 20.0 wt.-% ZrO$_2$.

3. Dental restoration according to claim 1, wherein the lithium silicate glass ceramic comprises 8.0 to 20.0 wt.-% ZrO$_2$.

4. Dental restoration according to claim 1, wherein the lithium silicate glass ceramic comprises 8.0 to 18.0 wt.-% ZrO$_2$.

5. Dental restoration according to claim 1, wherein the lithium silicate glass ceramic comprises 10.0 to 16.0 wt.-% ZrO$_2$.

6. Dental restoration according to claim 1, wherein the lithium silicate glass ceramic comprises lithium metasilicate as a main crystal phase.

7. Dental restoration according to claim 1, wherein the lithium silicate glass ceramic comprises lithium disilicate as a main crystal phase.

8. Dental restoration according to claim 7, wherein the lithium silicate glass ceramic has a fracture toughness, measured as K$_{IC}$ value, of at least 1.5 MPa·m$^{0.5}$.

9. Dental restoration according to claim 1, wherein the lithium silicate glass ceramic comprises 55.0 to 71.0 wt.-% SiO$_2$.

10. Dental restoration according to claim 1, wherein the lithium silicate glass ceramic comprises 60.0 to 69.0 wt.-% SiO$_2$.

11. Dental restoration according to claim 1, wherein the lithium silicate glass ceramic comprises 9.0 to 17.0 wt.-% Li$_2$O.

12. Dental restoration according to claim 1, wherein the lithium silicate glass ceramic comprises 11.0 to 15.0 wt.-% Li$_2$O.

13. Dental restoration according to claim 1, wherein the lithium silicate glass ceramic comprises 0.5 to 12.0 wt.-% nucleating agent, wherein the nucleating agent is selected from P$_2$O$_5$, TiO$_2$, Nb$_2$O$_5$ and/or metals.

14. Dental restoration according to claim 1, wherein the lithium silicate glass ceramic comprises 2.5 to 7.0 wt.-% nucleating agent, wherein the nucleating agent is selected from P$_2$O$_5$, TiO$_2$, Nb$_2$O$_5$ and/or metals.

15. Dental restoration according to claim 1, wherein the lithium silicate glass ceramic comprises further alkali metal oxide in a quantity of 1.0 to 7.0, wherein the further alkali metal oxide is selected from K$_2$O, Cs$_2$O and/or Rb$_2$O.

16. Dental restoration according to claim 1, wherein the lithium silicate glass ceramic comprises further alkali metal oxide in a quantity of 2.0 to 5.0, wherein the further alkali metal oxide is selected from K$_2$O, Cs$_2$O and/or Rb$_2$O.

17. Dental restoration according to claim 1, wherein the lithium silicate glass ceramic comprises up to 5.0 wt.-% alkaline earth metal oxide, wherein the alkaline earth metal oxide is CaO, BaO, MgO and/or SrO.

18. Dental restoration according to claim 1, wherein the lithium silicate glass ceramic comprises 0.2 to 10.0 wt.-% oxide of trivalent elements, wherein the oxide of trivalent elements is Al$_2$O$_3$, Y$_2$O$_3$, La$_2$O$_3$, and/or Bi$_2$O$_3$.

19. Dental restoration according to claim 1, wherein the lithium silicate glass ceramic comprises 2.5 to 7.0 wt.-% oxide of trivalent elements, wherein the oxide of trivalent elements is Al$_2$O$_3$, Y$_2$O$_3$, La$_2$O$_3$, and/or Bi$_2$O$_3$.

20. Dental restoration according to claim 1, wherein the lithium silicate glass ceramic comprises 2.5 to 3.5 wt.-% oxide of trivalent elements.

21. Dental restoration according to claim 20, wherein the oxide of trivalent elements comprises Al$_2$O$_3$, Y$_2$O$_3$, La$_2$O$_3$, and/or Bi$_2$O$_3$.

22. Dental restoration according to claim 1, wherein the lithium silicate glass ceramic comprises at least one further oxide of tetravalent elements selected from SnO$_2$ or GeO$_2$.

23. Dental restoration according to claim 1, wherein the lithium silicate glass ceramic comprises at least one further oxide of pentavalent elements.

24. Dental restoration according to claim 23, wherein at least one the oxide of pentavalent elements is Bi$_2$O$_5$.

25. Dental restoration according to claim 23, wherein the lithium silicate glass ceramic comprises at least one oxide of hexavalent elements selected from WO$_3$ or MoO$_3$.

26. Dental restoration according to claim 1, wherein the lithium silicate glass ceramic comprises at least one of the following components:

| Component | wt.-% |
|---|---|
| SiO$_2$ | 55.0 to 71.0 |
| Li$_2$O | 9.0 to 17.0 |
| K$_2$O | 1.0 to 5.0 |
| Al$_2$O$_3$ | 0.5 to 5.0 |
| P$_2$O$_5$ | 0.5 to 12.0 |
| ZrO$_2$ | 6.1 to 20.0 |

27. Dental restoration according to claim 1, wherein the lithium silicate glass ceramic comprises at least one of the following components:

| Component | wt.-% |
|---|---|
| SiO$_2$ | 55.0 to 71.0 |
| Li$_2$O | 9.0 to 17.0 |
| K$_2$O | 2.0 to 5.0 |
| Al$_2$O$_3$ | 2.5 to 3.5 |
| P$_2$O$_5$ | 2.5 to 7.0 |
| ZrO$_2$ | 8.0 to 20.0 |

28. Dental restoration according to claim 1, wherein the lithium silicate glass ceramic has a fracture toughness, measured as K$_{IC}$ value, of at least 1.8 MPa·m$^{0.5}$.

29. Dental restoration, which is coated with a lithium silicate glass, wherein the lithium silicate glass comprises at least 6.1 wt.-% ZrO$_2$.

30. Dental restoration according to claim 29, wherein the lithium silicate glass comprises nuclei suitable for forming lithium metasilicate and/or lithium disilicate crystals.

31. Dental restoration according to claim 1, wherein the lithium silicate glass ceramic comprises a nucleating agent selected from Pt, Pd, Au, Ag, or mixtures thereof.

32. Dental restoration according to claim 1, wherein the lithium silicate glass ceramic comprises at least 7.0 wt.-% $ZrO_2$.

33. Dental restoration according to claim 1, wherein the lithium silicate glass ceramic comprises at least 8.0 wt.-% $ZrO_2$.

34. Dental restoration according to claim 1, wherein the lithium silicate glass ceramic comprises at least 10.0 wt.-% $ZrO_2$.

35. Dental restoration according to claim 1, wherein the lithium silicate glass ceramic comprises 60.0 to 71.0 wt.-% $SiO_2$.

36. Process for coating a dental restoration, wherein a lithium silicate glass ceramic which comprises at least 6.1 wt.-% $ZrO_2$ is applied to the dental restoration and is subjected to a temperature in the range of 700 to 1200° C.

37. Process according to claim 36, wherein the lithium silicate glass ceramic is present in the form of a powder or a blank.

38. Process for coating a dental restoration, wherein a lithium silicate glass which comprises at least 6.1 wt.-% $ZrO_2$ is applied to the dental restoration and is subjected to a temperature in the range of 700 to 1200° C.

39. Process according to claim 38, wherein the lithium silicate glass is present in the form of a powder or a blank.

40. Process for coating a dental restoration, wherein a lithium silicate glass which comprises at least 6.1 wt.-% $ZrO_2$ and comprises nuclei suitable for forming lithium metasilicate and/or lithium disilicate crystals is applied to the dental restoration and is subjected to a temperature in the range of 700 to 1200° C.

41. Process according to claim 40, wherein the lithium silicate glass ceramic is prepared by a process in which a starting glass with the components of the lithium silicate glass ceramic is subjected to at least one heat treatment in the range of from 450 to 950° C.

42. Process according to claim 40, wherein the lithium silicate glass is prepared by a process in which a starting glass with the components of the lithium silicate glass is subjected to at least one heat treatment in the range of from 450 to 950° C.

43. Process for coating a zirconium oxide ceramic, wherein a lithium silicate glass ceramic which comprises at least 6.1 wt.-% $ZrO_2$ is applied to the zirconium oxide ceramic and is subjected to a temperature in the range of 700 to 1200° C.

44. Process for coating a zirconium oxide ceramic wherein a lithium silicate glass which comprises at least 6.1 wt.-% $ZrO_2$ is applied to the zirconium oxide ceramic and is subjected to a temperature in the range of 700 to 1200° C.

45. Process for coating a zirconium oxide ceramic, wherein a lithium silicate glass which comprises at least 6.1 wt.-% $ZrO_2$ and comprises nuclei suitable for forming lithium metasilicate and/or lithium disilicate crystals is applied to the zirconium oxide ceramic and is subjected to a temperature in the range of 700 to 1200° C.

* * * * *